United States Patent
Ittner et al.

(10) Patent No.: US 12,397,035 B2
(45) Date of Patent: Aug. 26, 2025

(54) COMPOSITIONS AND METHODS FOR TREATMENT

(71) Applicant: Celosia Therapeutics Pty Ltd, Camberwell (AU)

(72) Inventors: Lars Ittner, North Ryde (AU); Yazi Diana Ke, North Ryde (AU)

(73) Assignee: Celosia Therapeutics Pty Ltd, Camberwell (AU)

( * ) Notice: Subject to any disclaimer, the term of this patent is extended or adjusted under 35 U.S.C. 154(b) by 739 days.

(21) Appl. No.: 17/633,146

(22) PCT Filed: Aug. 12, 2020

(86) PCT No.: PCT/AU2020/050833
§ 371 (c)(1),
(2) Date: Feb. 4, 2022

(87) PCT Pub. No.: WO2021/026601
PCT Pub. Date: Feb. 18, 2021

(65) Prior Publication Data
US 2022/0347258 A1 Nov. 3, 2022

(30) Foreign Application Priority Data

Aug. 12, 2019 (AU) ................................ 2019902892
Jun. 1, 2020 (AU) ................................ 2020901796

(51) Int. Cl.
*A61K 38/08* (2019.01)
*A61P 25/28* (2006.01)

(52) U.S. Cl.
CPC .............. *A61K 38/08* (2013.01); *A61P 25/28* (2018.01)

(58) Field of Classification Search
None
See application file for complete search history.

(56) References Cited

U.S. PATENT DOCUMENTS

| 9,290,733 B2 | 3/2016 | Edgerton |
| 2011/0183341 A1 | 7/2011 | Yacoubian et al. |
| 2016/0220649 A1* | 8/2016 | Roodveldt Catellani .................. A61K 2239/38 |

FOREIGN PATENT DOCUMENTS

| WO | WO 2004/050870 A2 | 6/2004 |
| WO | WO 2011/120082 A1 | 10/2011 |
| WO | WO 2013/061163 A2 | 5/2013 |
| WO | WO 2015/118115 A1 | 8/2015 |

OTHER PUBLICATIONS

Cleveland Clinic (downloaded from URL:<Neurodegenerative Diseases: What They Are & Types (clevelandclinic.org)>) (Year: 2024).*
Banaszynski, Laura A. et al. "A Rapid, Reversible, and Tunable Method to Regulate Protein Function in Living Cells Using Synthetic Small Molecules" Cell, Sep. 2006, pp. 995-1004, vol. 126.
Chu, Ting-Ting et al., "Specific Knockdown of Endogenous Tau Protein by Peptide-Directed Ubiquitin-Proteasome Degradation" Cell Chemical Biology, 2016, pp. 453-461, vol. 23.
Gao, Na et al., "TDP-43 specific reduction induced by Di-hydrophobic tags conjugated peptides" Bioorganic Chemistry, 2019, pp. 254-259, vol. 84.
International Search Report for PCT/AU2020/050833 dated Sep. 25, 2020.
Bi, Mian et al., "Tau exacerbates excitotoxic brain damage in an animal model of stroke" Nature Communications, Jul. 2017, pp. 1-15, vol. 8, No. 473.
Deverman, Benjamin E. et al., "Cre-dependent selection yields AAV variants for widespread gene transfer to the adult brain" Nat Biotechnol., Feb. 2016, pp. 204-209, vol. 34, No. 2.
Eersel, J. Van et al., "Early-onset axonal pathology in a novel P301S-Tau transgenic mouse model of frontotemporal lobar degeneration" Neuropathology and Applied Neurobiology, 2015, pp. 906-925, vol. 41.
Hummel, Annika Van et al., "Selective Spatiotemporal Vulnerability of Central Nervous System Neurons to Pathologic TAR DNA-Binding Protein 43 in Aged Transgenic Mice" The American Journal of Pathology, Jun. 2018, pp. 1447-1456, vol. 188, No. 6, Jun. 2018.
Ittner, Lars M. et al., "The N-Terminal Extracellular Domain 23-60 of the Calcitonin Receptor-Like Receptor in Chimeras with the Parathyroid Hormone Receptor Mediates Association with Receptor Activity-Modifying Protein 1" Biochemistry, 2005, pp. 5749-5754, vol. 44.
Ittner, Lars M. et al., "Phosphorylated Tau Interacts with c-Jun N-terminal Kinase-interacting Protein 1 (JIP1) in Alzheimer Disease" The Journal of Biological Chemistry, Jul. 2009, pp. 20909-20916, vol. 284, No. 31.
Ke, Yazi et al., "Tau-Mediated Nuclear Depletion and Cytoplasmic Accumulation of SFPQ in Alzheimer's and Pick's Disease" PLoS One, Apr. 2012, pp. 1-8, vol. 7, Issue 4, e35678.
Ke, Yazi et al., "Short-term suppression of A315T mutant human TDP-43 expression improves functional deficits in a novel inducible transgenic mouse model of FTLD-TDP and ALS" Acta Neuropathol, Oct. 2015.
Shenouda, Marc et al., "Mechanisms Associated with TDP-43 Neurotoxicity in ALS/FTLD" Adv Neurobiol, 2018, pp. 239-263, vol. 20.

(Continued)

*Primary Examiner* — Sergio Coffa
(74) *Attorney, Agent, or Firm* — KNOBBE MARTENS OLSON & BEAR LLP

(57) ABSTRACT

Provided herein are methods for treating or preventing, or ameliorating at least one symptom of, a neurodegenerative disease associated with TDP-43 pathology, comprising administering to a subject an effective amount of a peptide comprising or consisting of the amino acid sequence of SEQ ID NO:1 or a conservative variant thereof, optionally linked to a protein destabilization domain sequence, or a nucleic acid molecule encoding said peptide. Also provided is a peptide comprising or consisting of the amino acid sequence of SEQ ID NO:1 or a conservative variant thereof, a chimeric molecule comprising said peptide linked to a protein destabilization domain sequence, and a polynucleotide encoding said peptide or chimeric molecule.

22 Claims, 11 Drawing Sheets
Specification includes a Sequence Listing.

(56) References Cited

OTHER PUBLICATIONS

Winton, Matthew J. et al., "Disturbance of Nuclear and Cytoplasmic TAR DNA-binding Protein (TDP-43) Induces Disease-like Redistribution, Sequestration, and Aggregate Formation" The Journal of Biological Chemistry, May 2008, pp. 13302-13309, vol. 283, No. 19.
Cai, Bin et al., "Research Progress of the Relationship of the Expression of TAR DNA/RNA-binding Domain Protein 43 in Neurodegenerative Disease and Brain Injury" Journal of Kunming Medical University, 2018, pp. 124-127, vol. 39, No. 5.
Buratti, Emanuele "TDP-43 post-translational modifications in health and disease" Expert Opinion on Therapeutic Targets, 2018, pp. 279-293, vol. 22, No. 3.
Prasad, Archana et al., "Molecular Mechanisms of TDP-43 Misfolding and Pathology in Amyotrophic Lateral Sclerosis" Frontiers in Molecular Neuroscience, Feb. 2019, pp. 1-36, vol. 12, Article 25.
Umahara, Takahiko et al., "14-3-3 eta isoform colocalizes TDP-43 on the coarse granules in the anterior horn cells of patents with sporadic amyotrophic lateral sclerosis" Brain Research, 2016, pp. 132-138, vol. 1646.

\* cited by examiner

```
             135                                      164
14-3-3θ    GDDRKQIIDNSQGAYQEAFDISKKEMQPTH
14-3-3η    GEKKNSVVEASEAAYKEAFEISKEQMQPTH
14-3-3γ    GEKRATVVESSEKAYSEAHEISKEHMQPTH
14-3-3σ    GDDKKRIIDSARSAYQEAMDISKKEMPPTN
14-3-3ζ    GDDKKGIVDQSQQAYQEAFEISKKEMQPTH
14-3-3ε    GNDRKEAAENSLVAYKAASDIAMTELPPTH
14-3-3β    GDNKQTTVSNSQQAYQEAFEISKKEMQPTH
            *:.:      . :  **. * :*:    : **:
```

A

B

A

B

A

B

A

B

COMPOSITIONS AND METHODS FOR TREATMENT

CROSS REFERENCE TO RELATED APPLICATIONS

This application is a U.S. National Phase Application of PCT International Application Number PCT/AU2020/050833, filed on Aug. 12, 2020, designating the United States of America and published in the English language, which is an International Application of and claims the benefit of priority to Australian Patent Application No. 2019902892, filed on Aug. 12, 2019, and Australian Patent Application No. 2020901796, filed on Jun. 1, 2020. The disclosures of the above-referenced applications are hereby expressly incorporated by reference in their entireties.

Reference to Sequence Listing

A Sequence Listing submitted as an ASCII text file via EFS-Web is hereby incorporated by reference in accordance with 37 U.S.C. § 1.52 (e). The name of the ASCII text file for the Sequence Listing is SeqList-DAVI588-001APC.txt, the date of creation of the ASCII text file is Feb. 4, 2022, and the size of the ASCII text file is 7 KB.

FIELD OF THE ART

The present disclosure relates to compositions and methods for the treatment and prevention of neurodegenerative diseases characterised by or associated with TDP-43 pathology. The disclosure also relates to isolated peptides and chimeric molecules, and to nucleic acids and genetic constructs encoding said peptides and chimeric molecules, that are suitable for treating and preventing said neurodegenerative diseases.

BACKGROUND

Amyotrophic lateral sclerosis (ALS) is a motor neuron disease affecting motor neurons in both the brain and the spinal cord. ALS is a fatal disease characterized by a loss of pyramidal cells in the cerebral motor cortex, anterior spinal motor neurons and brain stem motor neurons causing muscle weakness and atrophy. ALS typically shows rapid deterioration after onset, often leading to death within a few years.

Frontotemporal dementia (FTD) is characterised by progressive damage to the frontal and/or temporal lobes of the brain and is associated with progressive deterioration of decision-making abilities, control of behaviour and language. FTD is one of the most common forms of presenile dementia, with median life expectancy after diagnosis of less than 15 years.

ALS and FTD are both rapidly progressive and fatal neurodegenerative diseases with significant clinical, genetic and pathological overlap. ALS and FTD are typically classified as either familial (approximately 10% of cases, where one or more defined genetic mutations are implicated) or sporadic (approximately 90% of cases, in which etiology is typically not well understood). Familial and sporadic forms of the diseases are clinically indistinguishable. ALS and FTD are neuropathologically characterized by deposition of TDP-43 in neurons. Current research suggests that mislocalization of nuclear TDP-43 to the cytoplasm triggers toxic events including aberrant phosphorylation and fragmentation of TDP-43 (Shenouda et al., 2018, *Adv Neurobiol* 20:239-263). However the molecular mechanisms that regulate physiological nucleo-cytoplasmic shuttling of TDP-43 during mRNA processing and drive cytoplasmic accumulation in disease remain unknown.

There are no cures for ALS or FTD. Prognosis is poor and treatments are limited. There is a clear need for the development of new methods for treating these debilitating diseases.

SUMMARY OF THE DISCLOSURE

The present disclosure is predicated on the inventors' identification of 14-3-3θ as a novel interaction partner of TDP-43 that contributes to aberrant cytoplasmic localization of TDP-43 and to ALS and FTD pathogenesis. The inventors have found that pathological TDP-43 can be targeted and cleared using specific peptides derived from 14-3-3θ, reversing functional deficits associated with ALS and FTD.

A first aspect of the present disclosure provides a method for treating or preventing, or ameliorating at least one symptom of, a neurodegenerative disease associated with TDP-43 pathology, the method comprising administering to a subject in need thereof an effective amount of a peptide comprising or consisting of the amino acid sequence of SEQ ID NO:1 or a conservative variant thereof, or a nucleic acid molecule encoding said peptide.

In a particular embodiment, the neurodegenerative disease is selected from amyotrophic lateral sclerosis (ALS) and frontotemporal dementia (FTD). The ALS may be familial ALS or sporadic ALS. The FTD may be familial FTD or sporadic FTD. The at least one symptom may comprise, for example, disinhibition, hyperactivity, motor deficits or reduced muscle strength.

The amino acid sequence of SEQ ID NO:1 may be provided within a larger contiguous peptide or polypeptide sequence. In an exemplary embodiment, the peptide sequence may comprise or consist of the amino acid sequence of SEQ ID NO:2, a conservative variant thereof or a sequence at least about 75% identical to the sequence of SEQ ID NO:2.

The nucleic acid molecule encoding the peptide of SEQ ID NO:1 or a conservative variant thereof may comprise the nucleotide sequence of SEQ ID NO:4 or a nucleotide sequence at least about 70% identical to the sequence of SEQ ID NO:4.

The nucleic acid molecule encoding the peptide of SEQ ID NO:2, a conservative variant thereof or a sequence at least about 75% identical thereto may comprise the nucleotide sequence of SEQ ID NO:5 or a nucleotide sequence at least about 70% identical to the sequence of SEQ ID NO:5.

In a particular embodiment, the peptide comprises or is linked to a protein destabilization domain sequence. In an exemplary embodiment the protein destabilization domain sequence comprises the rapamycin-binding protein FKBP12.

Accordingly, in an embodiment the method comprises administering to the subject a genetic construct encoding a peptide comprising or consisting of the sequence of SEQ ID NO:1 or a conservative variant thereof operably linked to a nucleotide sequence encoding a protein destabilization domain.

A second aspect of the present disclosure provides the use of a peptide comprising or consisting of the amino acid sequence of SEQ ID NO:1 or a conservative variant thereof, or a nucleic acid molecule encoding said peptide, in the manufacture of a medicament for the treatment or prevention of, or amelioration of at least one symptom of, a neurodegenerative disease associated with TDP-43 pathology.

A third aspect of the present disclosure provides an isolated peptide comprising or consisting of the amino acid sequence of SEQ ID NO:1 or a conservative variant thereof.

The peptide may comprise or consist of the amino acid sequence of SEQ ID NO:2, a conservative variant thereof or a sequence at least about 75% identical to the sequence of SEQ ID NO:2.

A fourth aspect of the present disclosure provides an isolated polynucleotide encoding a peptide of the third aspect.

The polynucleotide may comprise or consist of the sequence of SEQ ID NO:4 or SEQ ID NO:5 or a polynucleotide at least about 70% identical to the sequence of SEQ ID NO:4 or SEQ ID NO:5.

In exemplary embodiments of the third and fourth aspects the peptide or polynucleotide is for use in the treatment or prevention of, or amelioration of at least one symptom of, a neurodegenerative disease associated with TDP-43 pathology.

A fifth aspect of the present disclosure provides a chimeric molecule comprising a peptide comprising or consisting of the amino acid sequence of SEQ ID NO:1 or a conservative variant thereof linked to a protein destabilization domain sequence.

A sixth aspect of the present disclosure provides an isolated polynucleotide encoding a chimeric molecule of the fifth aspect.

In exemplary embodiments of the fifth and sixth aspects the chimeric molecule or polynucleotide is for use in the treatment or prevention of, or amelioration of at least one symptom of, a neurodegenerative disease associated with TDP-43 pathology.

A seventh aspect of the present disclosure provides a vector comprising a polynucleotide sequence of the fourth or sixth aspect.

The vector may be a viral vector. The viral vector may be an AAV vector. Typically the vector is for administration to a subject for the treatment or prevention of, or amelioration of at least one symptom of, a neurodegenerative disease associated with TDP-43 pathology.

The vector may be designed for introduction into neurons or brain cells and to direct or facilitate expression of the encoded peptide or chimeric molecule in neurons or brain cells.

BRIEF DESCRIPTION OF THE DRAWINGS

Aspects and embodiments of the present disclosure are described herein, by way of non-limiting example only, with reference to the following drawings.

Figure 1:
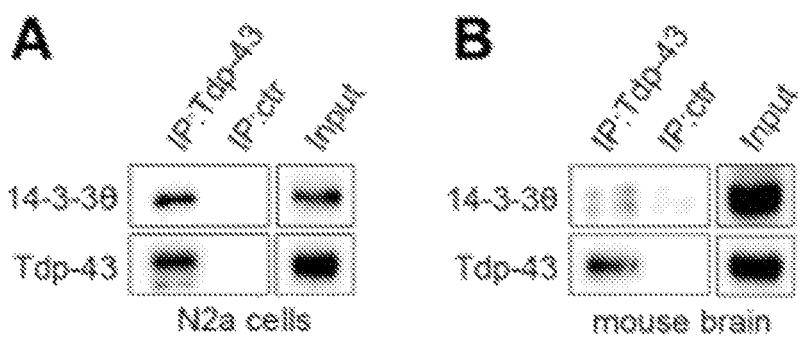
FIG. 1. 14-3-3θ interacts with TDP-43. Immunoprecipitation (IP) of 14-3-3θ/TDP-43 complexes from N2a cells (A) and mouse brain (B). Control (ctr) IP confirmed absence of unspecific binding.

Amino acid and nucleotide sequences are referred to by a sequence identifier number (SEQ ID NO). Sequences are provided in the Sequence Listing. The amino acid sequence set forth in SEQ ID NO: 1 represents an 11 amino acid motif from the αhelix 6 (αF) of human 14-3-3θ, and the DNA sequence encoding this motif is set forth in SEQ ID NO:4. The amino acid sequence set forth in SEQ ID NO:2 represents a 30 amino acid region from αF of human 14-3-3θ, and the DNA sequence encoding this region is set forth in SEQ ID NO:5. The amino acid sequence of human 14-3-3θ is set forth in SEQ ID NO:3. Other nucleotide sequences, including primer sequences, used in the studies described in the examples are set forth in SEQ ID NOs:6 to 20.

DETAILED DESCRIPTION

Unless defined otherwise, all technical and scientific terms used herein have the same meaning as is commonly understood by one of skill in the art to which the disclosure belongs. All patents, patent applications, published applications and publications, databases, websites and other published materials referred to throughout the entire disclosure, unless noted otherwise, are incorporated by reference in their entirety. In the event that there is a plurality of definitions for terms, those in this section prevail. Where reference is made to a URL or other such identifier or address, it understood that such identifiers can change and particular information on the internet can come and go, but equivalent information can be found by searching the internet. Reference to the identifier evidences the availability and public dissemination of such information.

The articles "a" and "an" are used herein to refer to one or more than one (i.e., to at least one) of the grammatical object of the article. By way of example, "an element" means one element or more than one element.

In the context of this specification, the term "about," is understood to refer to a range of numbers that a person of skill in the art would consider equivalent to the recited value in the context of achieving the same function or result.

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

As used herein, the term "operably-linked" refers to a functional linkage between two elements, regardless of orientation or distance between the two elements such that the function of one element is controlled or affected by the other element. For example, operable linkage with reference to a promoter and nucleic acid sequence means that the transcription and expression of the nucleic acid sequence is under the control of, or driven by, the promoter. In another example in the context of the present disclosure operable linkage between two nucleotide sequences may result in physical linkage or coupling between the expressed encoded peptides or polypeptides thereby forming a chimeric molecule.

The term "optionally" is used herein to mean that the subsequently described feature may or may not be present or that the subsequently described event or circumstance may or may not occur. Hence the specification will be understood to include and encompass embodiments in which the feature is present and embodiments in which the feature is not present, and embodiments in which the event or circumstance occurs as well as embodiments in which it does not.

The term "peptide" means a polymer made up of amino acids linked together by peptide bonds. The term "polypeptide" may also be used to refer to such a polymer although in some instances a polypeptide may be longer (i.e. composed of more amino acid residues) than a peptide. Notwithstanding, the terms "peptide" and "polypeptide" may be used interchangeably herein.

As used herein the terms "treating", "treatment", "preventing", "prevention" and grammatical equivalents refer to any and all uses which remedy the stated neurodegenerative disease, prevent, retard or delay the establishment of the disease, or otherwise prevent, hinder, retard, or reverse the progression of the disease. Thus the terms "treating" and "preventing" and the like are to be considered in their broadest context. For example, treatment does not necessarily imply that a patient is treated until total recovery. Where the disease displays or a characterized by multiple symptoms, the treatment or prevention need not necessarily remedy, prevent, hinder, retard, or reverse all of said symptoms, but may prevent, hinder, retard, or reverse one or more of said symptoms.

As used herein the term "effective amount" includes within its meaning a non-toxic but sufficient amount or dose of an agent or compound to provide the desired effect. The exact amount or dose required will vary from subject to subject depending on factors such as the species being treated, the age, size, weight and general condition of the subject, the severity of the disease or condition being treated, the particular agent being administered and the mode of administration and so forth. Thus, it is not possible to specify an exact "effective amount". However, for any given case, an appropriate "effective amount" may be determined by one of ordinary skill in the art using only routine experimentation.

The term "subject" as used herein refers to mammals and includes humans, primates, livestock animals (e.g. sheep, pigs, cattle, horses, donkeys), laboratory test animals (e.g. mice, rabbits, rats, guinea pigs), performance and show animals (e.g. horses, livestock, dogs, cats), companion animals (e.g. dogs, cats) and captive wild animals. Preferably, the mammal is human or a laboratory test animal. Even more preferably, the mammal is a human.

TDP-43 is a multifunctional RNA/DNA binding protein encoded by the TARDBP gene. It harbors two RNA recognition motifs and a large C-terminal glycine-rich domain (GRD) that mediates protein-protein interactions. The G-rich domain contains the vast majority of pathogenic TARDBP mutations in familial ALS. However prior to the present invention little was known about the functional role of TDP-43 interactions in physiology and disease.

As exemplified herein, the inventors have identified the protein 14-3-3θ as a novel interaction partner of TDP-43. Pathogenic variants of TDP-43 show increased interaction with 14-3-3θ, resulting in cytoplasmic accumulation, insolubility, phosphorylation and fragmentation of TDP-43, resembling pathological changes in disease. Without wishing to be bound by theory, the inventors suggest that a transient interaction with 14-3-3θ may stabilise TDP-43 while it resides in the cytoplasm during RNA shuttling. The inventors further suggest that 14-3-3θ interacts with aberrant TDP-43 conformations and makes them prone to pathological modifications.

As also exemplified herein, the inventors demonstrate that use of a unique peptide sequence derived from 14-3-3θ mediates the removal of pathological TDP-43 from brains of mice, and reverses and prevents ALS and FTD-relevant symptoms. While exemplified herein in the context of this peptide sequence conjugated to a protein destabilization domain, the present disclosure contemplates the use of the peptide in the absence of the protein destabilization domain. Without wishing to be bound by theory, the inventors suggest that the peptide interferes with the physiological and/or pathological interaction between 14-3-3θ and TDP-43, thereby preventing toxic downstream effects of 14-3-3θ/TDP-43 complexes.

In one aspect the present disclosure provides a method for treating or preventing, or ameliorating at least one symptom of, a neurodegenerative disease associated with TDP-43 pathology, the method comprising administering to a subject in need thereof a peptide comprising or consisting of the amino acid sequence of SEQ ID NO:1 or a conservative variant thereof, or a nucleic acid molecule encoding said peptide.

Embodiments of the present disclosure are applicable to the treatment or prevention of any neurodegenerative disease that is characterized by, or otherwise associated with, TDP-43 pathology. Typically such diseases are characterized by or associated with cytoplasmic accumulation of nuclear TDP-43 and with aberrant phosphorylation and fragmentation of TDP-43. In particular embodiments, the disease is amyotrophic lateral sclerosis (ALS) or frontotemporal dementia (FTD). The ALS may be familial or sporadic ALS. The FTD may be familial or sporadic FTD.

Symptoms of the neurodegenerative disease include behavioural and physical deficits characteristic of or associated with the disease. Thus, in accordance with the present disclosure, the administration of the peptide or nucleic acid molecule encoding said peptide may improve one or more behavioural or physical deficits characteristic of or associated with the neurodegenerative disease. Such behavioural and physical deficits include disinhibition, hyperactivity, motor deficits and reduced muscle strength.

Numerous pathogenic variants of TDP-43 are known to be associated with sporadic or familial ALS and FTD, including for example A315T, N345K, M337V, G294A, A382T and G287S mutations. However those skilled in the art will recognise that the scope of the present disclosure is not limited to the treatment or prevention of neurodegenerative diseases in individuals harbouring one or more of these mutations.

The peptide RKQTIDNSQGA (SEQ ID NO:1) for use in accordance with aspects and embodiments of the present disclosure is an 11 amino acid motif present within αhelix 6 (αF) of human 14-3-3θ (corresponding to amino acid residues 138-148 of wild type human 14-3-3θ as set forth in SEQ ID NO:3).

Also contemplated herein are conservative variants of the peptide of SEQ ID NO:1. Conservative variants comprise one or more conservative amino acid substitutions, being the substitution or replacement of one amino acid for another amino acid with similar properties as would be well understood by those skilled in the art. For example, the substitution of the neutral amino acid serine (S) for the similarly neutral amino acid threonine (T) would be a conservative amino acid substitution. Those skilled in the art will be able to determine suitable conservative amino acid substitutions that do not eliminate the functional properties of the peptide with respect to TDP-43 interactions.

Accordingly, also provided herein is an isolated peptide comprising or consisting of the amino acid sequence of SEQ ID NO:1 or a conservative variant thereof. In the present context, the term "isolated" refers to As used herein, "isolated" with reference to a nucleic acid molecule means that the peptide is substantially free of cellular material or other contaminating proteins from the cells from which the peptide is derived (and thus altered from its natural state), or substantially free from chemical precursors or other chemicals when chemically synthesized, and thus altered from its natural state.

The peptide of SEQ ID NO:1 or a conservative variant thereof may be provided within a larger contiguous peptide or polypeptide sequence. A peptide sequence comprising the sequence of SEQ ID NO:1 may comprise, for example, about 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95 or 100 residues, typically as a contiguous sequence. By way of example, the peptide of SEQ ID NO:1, for use in accordance with the present disclosure, may be provided as part of the sequence of the αF helix of 14-3-3θ, such as the sequence comprising amino acids 135 to 164 (SEQ ID NO:2) of human 14-3-3θ (SEQ ID NO:3) or a portion thereof, or a sequence at least about 75% identical thereto. For example, the sequence of the αF helix comprising the sequence of SEQ ID NO:1 may be 12, 13, 14, 15, 16, 17, 18, 19, 20, 21, 22, 23, 24, 25, 26, 27, 28, 29, 30 or more amino acids in length.

In an embodiment, the peptide may comprise or consist of the amino acid sequence of SEQ ID NO:2, a conservative variant thereof or a sequence at least about 75% identical to the sequence of SEQ ID NO:2. The sequence may be about 75%, 80%, 85%, 90%, 91%, 92%, 93%, 94%, 95%, 96%, 97%, 98% or 99% identical to the sequence of SEQ ID NO:2. Accordingly, also provided herein is an isolated peptide comprising or consisting of the amino acid sequence of SEQ ID NO:2, a conservative variant thereof or a sequence at least about 75% identical to the sequence of SEQ ID NO:2.

A peptide comprising or consisting of the sequence of SEQ ID NO:1 or a conservative variant thereof may include or be linked to one or more other moieties to facilitate, for example, transport, cell recognition, targeting, or another function such as protein destabilisation or degradation. For example, the peptide may be linked to or contain a cell targeting moiety that facilitates targeting of the peptide to one or more particular types such as neurons or other cells of the central nervous system. Also by way of example, as described further hereinbelow, the peptide may contain or be linked to protein destabilisation or degradation signal or domain to disrupt stability and/or induce degradation in vivo. The peptide can be linked to the one or more other moieties by any method known in the art, including any chemical or recombinant method, where appropriate, resulting in the formation of covalent and/or non-covalent bonds between the molecule and the one or more other moieties. The moieties may be peptide, polypeptide or protein moieties. Thus, the disclosure further provides chimeric peptides, polypeptides and proteins containing the sequence RKQTIDNSQGA (SEQ ID NO:1) or a conservative variant thereof conjugated to a heterologous peptide, polypeptide or protein. Such a chimeric peptide, polypeptide or protein may have a length of, for example, up to about 15, 20, 25, 30, 35, 40, 45, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 1500 or 2000 residues or more.

The peptide of SEQ ID NO:1 or a conservative variant may be conjugated to the C-terminal or N-terminal end of the additional peptide, polypeptide or protein moiety. The component molecules can be conjugated using, for example, standard chemical coupling techniques such as MBS, glutaraldehyde, EDC, or BDB coupling, or may be linked by peptide synthesis methods or recombinant methods known to those skilled in the art.

In particular embodiments of the present disclosure the peptide comprising the sequence of SEQ ID NO:1 or a conservative variant thereof is conjugated to or contains a moiety providing a protein destabilisation or degradation signal. In exemplary embodiments the protein destabilisation or degradation signal is provided by a protein destabilisation or degradation domain (referred to herein for convenience as a "destabilization domain"). A "destabilization domain" refers to a protein, polypeptide or amino acid sequence that is capable of disrupting the stability, and optionally inducing degradation, of a peptide, polypeptide or protein of interest when functionally coupled to the peptide, polypeptide or protein of interest. Examples of destabilization domains well known to those skilled in the art include ubiquitin, PEST sequences (proline-, glutamic acid-, serine- and threonine-rich sequences), cyclin destruction boxes, hydrophobic stretches of amino acids and rampamycin-binding protein FKBP12 (such as found in the pTuner plasmid, Clontech). A suitable destabilization domain may be incorporated into a peptide sequence of the present disclosure or conjugated to the N- or C-terminal of the peptide with or without a linker. For embodiments in which it is desired to include a destabilization domain, those skilled in the art will appreciate that any suitable destabilization domain may be employed, and the scope of the present disclosure is not limited by reference to any specific destabilization domain.

Also provided herein are chimeric peptides, polypeptides and proteins comprising a peptide of SEQ ID NO:1 or a conservative variant thereof conjugated to a protein destabilization domain sequence. Also provided herein are chimeric peptides, polypeptides and proteins comprising a peptide of SEQ ID NO:2, a conservative variant thereof or a sequence at least about 75% identical to the sequence of SEQ ID NO:2 conjugated to a protein destabilization domain sequence.

Peptides and polypeptides disclosed herein can be produced using any method known in the art, including chemical synthesis techniques, nucleic acid synthesis techniques, peptide synthesis techniques and/or recombinant techniques. In one example a peptide, such as the peptide of SEQ ID NO:1, is synthesized using the Fmoc-polyamide mode of solid-phase peptide synthesis. Other synthesis methods include solid phase t-Boc synthesis and liquid phase synthesis. Purification can be performed by any one, or a combination of, techniques such as re-crystallization, size exclusion chromatography, ion-exchange chromatography, hydrophobic interaction chromatography and reverse-phase high performance liquid chromatography using, for example, acetonitrile/water gradient separation.

Alternatively, peptides and polypeptides may be produced using recombinant methods well known in the art. Nucleic acid encoding the peptides and polypeptides can be obtained by any suitable method, for example RT-PCR or synthesis of an oligonucleotide that encodes a polypeptide of the present invention. Accordingly, as described further below, also provided herein are nucleic acid molecules encoding peptides and polypeptides, including chimeric peptides and polypeptides disclosed herein. It is well within the skill of a skilled artisan to design a nucleic acid molecule(s) that encodes peptides and polypeptides, including chimeric peptides and polypeptides disclosed herein.

Peptidomimetics of the peptide sequences disclosed herein are also contemplated and encompassed by the present disclosure. The term "peptidomimetic," as used herein means a peptide-like molecule that has the ability of the peptide upon which it is structurally based to interact with TDP-43. Such peptidomimetics include chemically modified peptides, peptide-like molecules containing non-naturally occurring amino acids, and peptoids (see, for example, Goodman and Ro, Peptidomimetics for Drug Design, in "Burger's Medicinal Chemistry and Drug Discovery" Vol. 1 (ed. M. E. Wolff; John Wiley & Sons 1995), pages 803-861). A variety of peptidomimetics are known in the art including, for example, peptide-like molecules which contain a constrained amino acid (for example an α-methylated amino acid, α,α-dialkyl glycine, α-, β- or γ-aminocycloalkane carboxylic acid, an α,β-unsaturated amino acid, a β,β-dimethyl or β-methyl amino acid or other amino acid mimetic), a non-peptide component that mimics peptide secondary structure (for example a nonpeptidic 3-turn mimic, γ-turn mimic, a mimic of β sheet structure, or a mimic of helical structure), or an amide bond isostere (for example a reduced amide bond, methylene ether bond, ethylene bond, thioamide bond or other amide isostere). Methods for identifying peptidomimetics are also well known in the art and include, for example, the screening of databases that contain libraries of potential peptidomimetics.

The present disclosure also provides isolated nucleic acid molecules encoding peptides and chimeric peptides as described herein, as well as methods in which said nucleic acid molecules, typically as part of a vector or similar genetic construct, are administered to subjects in need thereof.

For example, the nucleic molecule encoding the peptide of SEQ ID NO:1 or a conservative variant thereof may comprise a nucleotide sequence as set forth in SEQ ID NO:4 or a sequence having at least or about 70%, 75%, 80%, 81%, 82%, 83%, 84%, 85%, 86%, 87%, 88%, 89%, 90%, 91%, 92%, 93%, 94%, 95%, 96%, 97%, 98% or 99% sequence identity to the sequence set forth in SEQ ID NO:4. For example, the nucleic molecule encoding the peptide of SEQ ID NO:2, a conservative variant thereof or a sequence having at least about 75% identity to the sequence of SEQ ID NO:2 may comprise a nucleotide sequence as set forth in SEQ ID NO:5 or a sequence having at least or about 70%, 75%, 80%, 81%, 82%, 83%, 84%, 85%, 86%, 87%, 88%, 89%, 90%, 91%, 92%, 93%, 94%, 95%, 96%, 97%, 98% or 99% sequence identity to the sequence set forth in SEQ ID NO:5. The nucleic acid molecules may further comprise the nucleotide sequence of a selected protein destabilization domain operably linked to the nucleotide sequences described above such that a chimeric peptide or polypeptide is expressed.

The present disclosure also provides vectors comprising one or more nucleotide sequences described herein. Typically the nucleotide sequence(s) is operably linked to a promoter to allow for expression of the peptide or polypeptide. The vectors can be episomal vectors (i.e., that do not integrate into the genome of a host cell), or can be vectors that integrate into a host cell genome. Vectors may be replication competent or replication-deficient. Exemplary vectors include, but are not limited to, plasmids, cosmids, and viral vectors, such as adeno-associated virus (AAV) vectors, lentiviral, retroviral, adenoviral, herpesviral, parvoviral and hepatitis viral vectors. The choice and design of an appropriate vector is within the ability and discretion of one of ordinary skill in the art.

Provided herein are polynucleotides that comprise expression cassettes or expression constructs that can be used for the expression of a peptide, polypeptide or chimeric peptide or polypeptide as described herein in a suitable vector, for use in gene therapy. Thus, in particular embodiments, methods of the present disclosure comprise administering to a subject in need a vector comprising nucleotide sequences encoding peptides and polypeptides disclosed herein, typically operably linked to a heterologous promoter such that the peptide, polypeptide, or chimeric peptide or polypeptide of interest is expressed in vivo. In particular exemplary embodiments the vector is a viral vector. As used herein, the term "viral vector" refers to a vector derived from any virus and typically includes at least one element of origin and has the capacity to be packaged into a recombinant virus or virion. Viral vectors can have one or more of the wild-type genes of the virus from which the vector is derived deleted in whole or part, but retain functional flanking ITR sequences, which are necessary for the rescue, replication and packaging of the virion. Thus, a viral vector typically includes at least those sequences required in cis for replication and packaging (e.g., functional ITRs) of the virus. The ITRs need not be the wild-type nucleotide sequences, and may be altered, e.g., by the insertion, deletion or substitution of nucleotides, as long as the sequences provide for functional rescue, replication and packaging. The vector and/or virion can be utilized for the purpose of transferring heterologous sequences into cells either in vitro or in vivo.

In particular embodiments the vector is an AAV vector, i.e. a vector derived from an adeno-associated virus, including without limitation, AAV1, AAV2, AAV3, AAV4, AAV5, AAV6, AAV7, AAV8, AAV9, AAV10, AAV11, AAV12 or AAV13, or using synthetic or modified AAV capsid proteins such as those optimised for efficient in vivo transduction, for example of the central nervous system. A recombinant AAV vector describes replication-defective virus that includes an AAV capsid shell encapsidating an AAV genome. Typically, one or more of the wild-type AAV genes have been deleted from the genome in whole or part, preferably the rep and/or cap genes. Functional ITR sequences are necessary for the rescue, replication and packaging of the vector genome into the rAAV virion.

AAV ITRs may be derived from any of several AAV serotypes, including without limitation, AAV1, AAV2, AAV3, AAV4, AAV5, AAV6, AAV7, AAV8, AAV9, AAV10, AAV11, AAV12, AAV13, etc., or may be synthetic. The skilled addressee can make the selection without undue experimentation. AAV ITRs are typically about 145 nucleotides in length, although need not have a wild-type nucleotide sequence, i.e. may be altered by the insertion, deletion and/or substitution of nucleotides, provided they are functional. Furthermore, the ITRs in the polynucleotide need not necessarily be the same or derived from the same AAV serotype or isolate, so long as they function as intended, i.e., assist in the rescue, replication and packaging a transgene. The nucleotide sequences of AAV ITRs are well known in the art.

The vectors for use in accordance with the present disclosure can also include transcriptional enhancers, translational signals, and transcriptional and translational termination signals. Examples of transcriptional termination signals include, but are not limited to, polyadenylation signal sequences, such as bovine growth hormone (BGH) poly(A), SV40 late poly(A), rabbit beta-globin (RBG) poly(A), thymidine kinase (TK) poly(A) sequences, and any variants thereof. In some embodiments, the transcriptional termination region is located downstream of the posttranscriptional regulatory element. In some embodiments, the transcriptional termination region is a polyadenylation signal sequence.

The vectors for use in accordance with the present disclosure can also include various posttranscriptional regulatory elements. In some embodiments, the posttranscriptional regulatory element can be a viral posttranscriptional regulatory element. Non-limiting examples of viral posttranscriptional regulatory element include woodchuck hepatitis virus posttranscriptional regulatory element (WPRE), hepatitis B virus posttranscriptional regulatory element (HBVPRE), RNA transport element, and any variants thereof.

The present disclosure contemplates the delivery of peptides, polypeptides, polynucleotides and vectors to subjects in need of treatment by any suitable means, and typically in the form of pharmaceutical compositions, which compositions may comprise one or more pharmaceutically acceptable carriers, excipients or diluents. Such compositions may be administered in any convenient or suitable route such as by parenteral (e.g. intraperitoneal, subcutaneous, intraarterial, intravenous, intramuscular), oral (including sublingual), nasal or topical routes. In circumstances where it is required that appropriate concentrations of the molecules are delivered directly to the site in the body to be treated, administration may be regional rather than systemic. Regional administration provides the capability of delivering very high local concentrations of the molecules to the required site and thus is suitable for achieving the desired therapeutic or preventative effect whilst avoiding exposure of other organs of the body to the vectors and molecules and thereby potentially reducing side effects.

It will be understood that the specific dose level of a composition of the invention for any particular subject will depend upon a variety of factors including, for example, the activity of the specific agents employed, the age, body weight, general health and diet of the individual to be treated, the time of administration, rate of excretion, and combination with any other treatment or therapy. Single or multiple administrations can be carried out with dose levels and pattern being selected by the treating physician. A broad range of doses may be applicable. Considering a patient, for example, from about 0.1 mg to about 1 mg of agent may be administered per kilogram of body weight per day. Dosage regimens may be adjusted to provide the optimum therapeutic response. For example, several divided doses may be administered daily, weekly, monthly or other suitable time intervals or the dose may be proportionally reduced as indicated by the exigencies of the situation.

Examples of pharmaceutically acceptable carriers or diluents are demineralised or distilled water; saline solution; vegetable based oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

The present invention contemplates combination therapies, wherein peptides, polypeptides, polynucleotides and vectors as described herein are coadministered with other suitable agents that may facilitate the desired therapeutic or prophylactic outcome. By "coadministered" is meant simultaneous administration in the same formulation or in two different formulations via the same or different routes or sequential administration by the same or different routes. By "sequential" administration is meant a time difference of from seconds, minutes, hours or days between the administration of the agents. Administration may be in any order.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The present disclosure will now be described with reference to the following specific examples, which should not be construed as in any way limiting the scope of the disclosure.

Examples

The following examples are illustrative of the disclosure and should not be construed as limiting in any way the general nature of the disclosure of the description throughout this specification.

General Methods

Bacterial two-hybrid screening. BacterioMatch II two hybrid system was performed in accordance with the manufacturer's instructions (Chem-Agilent). Briefly, the carboxyl-terminal part of human TDP-43 (corresponding to amino acids 259-415 of the human TDP-43 sequence of UniProt Accession No. Q13148) was cloned into the pBT (bait) vector and used to identify interacting partners from a human brain cDNA pTRG plasmid library. Detection of protein-protein interaction partners was based on transcriptional activation of the HIS3 reporter gene and positives were further verified by a secondary streptomycin resistance reporter. All propagations and transformations were done using the chemically-competent cells provided within the kit. Colonies were visualized for images by incubation of growth plates with 2% TTC/PBS (Sigma) for 10 min at 37° C.

Cloning. Point mutations and truncation variants were generated by standard site-directed mutagenesis (Ittner et al., 2005, *Biochemistry* 44: 5749-5754). Knockdown of 14-3-3θ was carried out using the 14-3-3θ MISSION shRNA lentiviruses (Sigma-Aldrich) with sequence CCGGCAGTTGCTTAGAGACAACCTACTCGAGTAGGTTGTCTCTAAGCAACTGTT TTTG (SEQ ID NO:6). Stable overexpression of 14-3-3θ (C-terminal V5-tag) in SH-SY5Y cells was achieved using lentiviruses (cloning vector pLenti6/Ubc; Life Technologies). All 14-3-3 isoforms were cloned with a C-terminal myc tag into pcDNA3.1/myc (Life Technologies) and TDP-43 wild-type/mutants were cloned with a C-terminal V5 tag into pcDNA3.1/V5 (Life Technologies) for immunoprecipitation.

Adeno-associated viruses. 14-3-3θ (V5-tagged) was cloned into a rAAV vector under the human synapsin promoter using the plasmid pAAV-hSyn-EGFP (Addgene, #50465) as backbone and removing EGFP. The same vector or a variant for mCherry expression was used as control. Packaging of rAAV9 vectors were performed as previously described (Bi et al., 2017, *Nat Commun* 8: 473) using the capsid AAV9.PHP.B (Deverman et al., 2016, *Nat Biotechnol* 34: 204-209). 2 µl of rAAV ($1\times10^{13}$ viral genomes/ml) was injected into the hippocampus (−1.94 mm AP, 1.6 mmML, 1.8 mm DV from lambda) of 3 months old wild-type or iTDP-43$^{A315T}$ mice (Ke et al., 2015, *Acta Neuropathol* 130: 661-678). For spinal cord injections, 1 ul of rAAV ($1\times10^{13}$ viral genomes/ml) was injected directly into the spinal cord of cryo-anaesthetized neonatal pups (P0-2). All animal experiments have been approved by the Macquarie University Animal Ethics Committee.

Immunoprecipitation. Immunoprecipitation was performed as previously described (Ittner et al., 2009, *J Biol Chem* 284: 20909-20916). Briefly, 293T HEK cells were co-transfected with variants of TDP-43 in pcDNA3.1/V5 and/or 14-3-3 isoforms/variants. Cells were lysed in RIPA buffer. Equal amounts of proteins were incubated overnight with 1 ul of V5 antibody (Life Technologies) and precipitated using magnetic Protein G beads (Life Technologies). Co-immunoprecipitation was further confirmed by Western blotting using myc antibodies.

Western blotting. Western blotting was performed as previously described (Ke et al., 2012, *PLoS One* 7: e35678). Primary antibodies used for immunoblotting were human TDP-43, c-terminal TDP-43, pan-TDP-43 (Proteintech), 14-3-3θ (Abcam), V5, myc (Life Technologies), phospho-TDP-43 S409/410 (Cosmobio), GAPDH (Merck-Millipore).

Cell culture and staining. All immunorecipitation experiments were carried out in 293T HEK cells. Cells were maintained in DMEM containing 10% fetal bovine serum (FBS) as per standard protocols. SH-SY5Y cells were maintained in DMEM/F-12 containing 10% FBS and used for 14-3-3θ overexpression or knockdown. Stable overexpression and knockdown of 14-3-3θ were achieved through lentiviral transduction. For immunocytochemistry, cells were fixed in 4% PFA and blocked with 3% heat-inactivated goat serum/2% BSA. Antibodies, V5 (Sigma), myc (Life Technologies) and secondary Alexa Fluor 488, 555 (Life Technologies) were used. Coverslips were mounted in Immun-Mount (Southern Biotech).

Microscopy. All cell culture fluorescence images were taken with either a BX51 epifluorescence or a confocal FV10i microscopes (Olympus).

In vitro complex assay. HEK293T cells were transfected with full length wild type TDP-43 or TDP-43 with F147L/F149L double mutations (both c-terminally V5-tagged) or 14-3-3θ (with poly-histidine-tag). Cells transfected with TDP-43 constructs were lysed in immunoprecipitation buffer (IPB) (20 mM of Tris-HCl (pH 7.8), 150 mM of NaCl, 0.1% (v/v) of NP-40) supplemented with EDTA-free Complete protease inhibitor cocktail (Roche) and V5-tagged TDP-43 was IPed (as above) with mouse anti-v5 antibody (Life Technologies). Subsequently, the lysate was washed twice with IPB, twice with DNase/RNase buffer (DRB) (10 mM Tris-HCl (pH 7.6), 2.5 mM of $MgCl_2$ and 0.5 mM of $CaCl_2$) and reconstituted in DRB. The 14-3-3θ-HIS transfected cells were lysed in IPB and purified via TALON resin (Clontech Laboratories). Briefly, the lysates were incubated with TALON resins for 2 h at 4° C., washed thrice with IPB and eluted in in vitro interaction buffer (IVIB) (20 mM Tris-HCl (pH 7.8), 0.1 M of NaCl, 20% (v/v) of glycerol, 5 mM of $MgCl_2$, 5 mM of $CaCl_2$, 0.1% (v/v) of NP-40, 1 mM of EDTA, 0.1 mM DTT and 0.2 mM of PMSF). For RNA and DNA digestions, the magnetic bead suspensions containing bound V5-tagged TDP-43 were incubated with either DNase, RNase or buffer (control) for 10 min at 37° C. After digestion, all the reaction mixtures were washed once with ice-cold IPB and resuspended in IVIB. The purified TDP-43 and 14-3-3θ were subsequently incubated for 2 h at 4° C. for in vitro interaction. The reaction was washed as per regular IP and eluted in 4x sample buffer for Western blotting.

Quantitative PCR. RNA purification and quantitative PCR was performed as previously described (Bi et al., 2017, *Nat Commun* 8: 473). Briefly, RNA was extracted from mouse cortical brain tissue using RNeasy Mini Kit (Qiagen), following the manufacturer's instructions. To remove contaminating genomic DNA, an on-column DNA-digest was performed with RNase-free DNase I (Qiagen). cDNA was synthesized from 2.5 μg of total RNA with the second strand cDNA-synthesis kit (Invitrogen). mRNA levels were determined by quantitative PCR, using a Fast SYBR green reaction mix (Invitrogen) and gene-specific primer pairs, using a M×3000 real-time PCR cycler (Stratagene). Levels were expressed as a fold change of the housekeeping gene Gapdh and converted to fold difference relative to control tissue. These primers were used (5' to 3'):

```
14-3-3θ
                                        (SEQ ID NO: 7)
(F):       GCTAAAACGGCTTTTGATGAGG;

(SEQ ID NO: 8)
(R):       GTGCCCTGGATGCCTTTAGTT 14-3-3β
                                        (SEQ ID NO: 9)
(F):       CTCCAGTCCTCCGCGAAAAT;

(SEQ ID NO: 10)
(R):       GAGAGTTCGTGTCCCTGCTC 14-3-3γ
                                        (SEQ ID NO: 11)
(F):       GGCGGTCTTCGGTTTCCTTC;

(SEQ ID NO: 12)
(R):       GTTCAGCTCGGTCACGTTCTT 14-3-ε
                                        (SEQ ID NO: 13)
(F):       CGCACCCCATTCGTTTAGG;

(SEQ ID NO: 14)
(R):       ATTCTGCTCTTCACCATCACC 14-3-3ζ
                                        (SEQ ID NO: 15)
(F):       CTACGATCACGTCCAACCCG;

(SEQ ID NO: 16)
(R):       GTCAAACGCTTCTGGCTGC 14-3-3σ
                                        (SEQ ID NO: 17)
(F):       ACAACCTGACACTGTGGACG;

(SEQ ID NO: 18)
(R):       CCTTTGGAGCAAGAACAGCG

Gapdh
                                        (SEQ ID NO: 19)
(F):       GTGAAGGTCGGTGTGAAC;

(SEQ ID NO: 20)
(R):       ATCTCCACTTTGCCACTGCAA
```

Mice. iTDP-43$^{A315T}$ mice have been previously described (Ke et al., 2015, *Acta Neuropathol* 130: 661-678). These mice constitutively express human A315T mutant TDP-43 under control of a doxycycline-controllable (Tet-OFF) promoter in CNS neurons. Mice were group housed on a 12 h light/dark cycle with ad libitum access to food and water. Time mated C57Bl/6 mice were obtained from ARC Perth. All animal experiments have been approved by the Macquarie University Animal Ethics Committee.

Motor Testing—Wire test was performed as previously described (van Hummel et al., 2018, *Am J Pathol* 188: 1447-1456). Briefly, mice were placed on a wire mesh and allowed to hang upside down, latency to fall off was recorded. Grip Strength was performed as previously described (*Am J Pathol* 188, 1447-1456) using a grip strength meter to measure peak forearm strength (Chatillon, AMETEK).

Immunohistochemistry. Staining of paraffin tissue sections, including antigen retrieval has been described previously (van Eersel et al., 2015, *Neuropathology and Applied Neurobiology* 41: 906-925). Primary antibodies used for staining were against human TDP-43, pan-TDP-43 (ProteinTech). NeuN, mCherry, EGFP (Abcam), V5 (Sigma). Secondary antibodies used were Alexa-Fluor coupled 488, 555 and 647 (Life Technologies).

Statistical analysis. Statistical analysis was performed with GraphPad Prism 6.0. Student's t-tests were used for comparing two groups, and ANOVA for multi group comparison.

Example 1—Identification of a Novel Interaction Partner of TDP-43

To identify novel interaction partners of the C-terminal glycine-rich domain (GRD) of TDP-43 the inventors performed a bacterial two-hybrid screen as described above.

The best candidate identified (11 of 65 hits) was 14-3-3θ (encoded by the YWHAQ gene), a member of the 14-3-3 scaffolding protein family. Co-immunoprecipitation from murine N2a cells and mouse brains confirmed interaction between endogenous 14-3-3θ and TDP-43 (FIG. 1).

Figure 2:
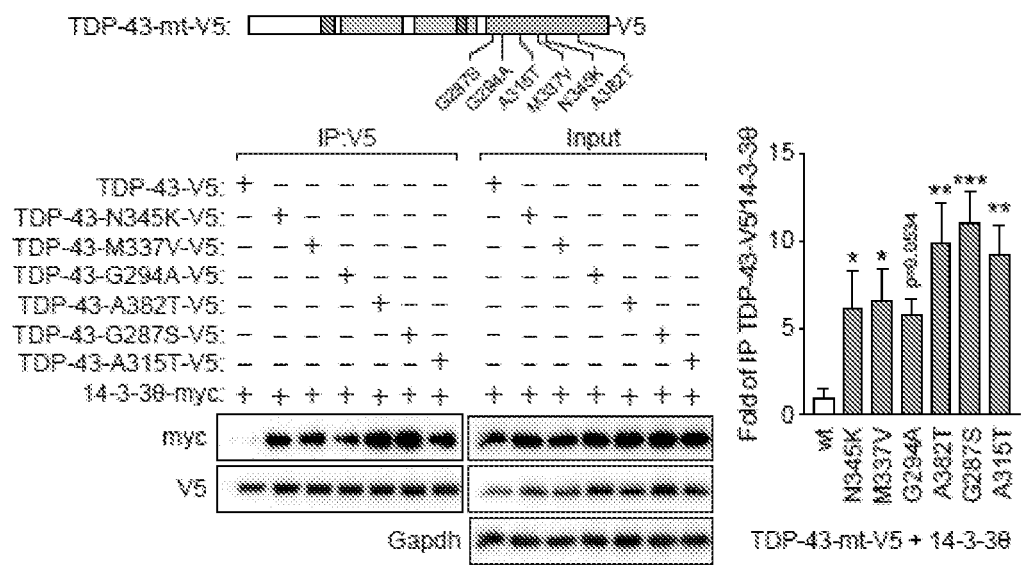
FIG. 2. Co-expression shows significantly enhanced immunoprecipitation (IP) of 14-3-3θ with TDP-43 carrying pathogenic mutations compared to its non-mutant form (n=3). *P<0.001;P<0.01;*P<0.05. Error bars indicate SEM.
Figure 3:
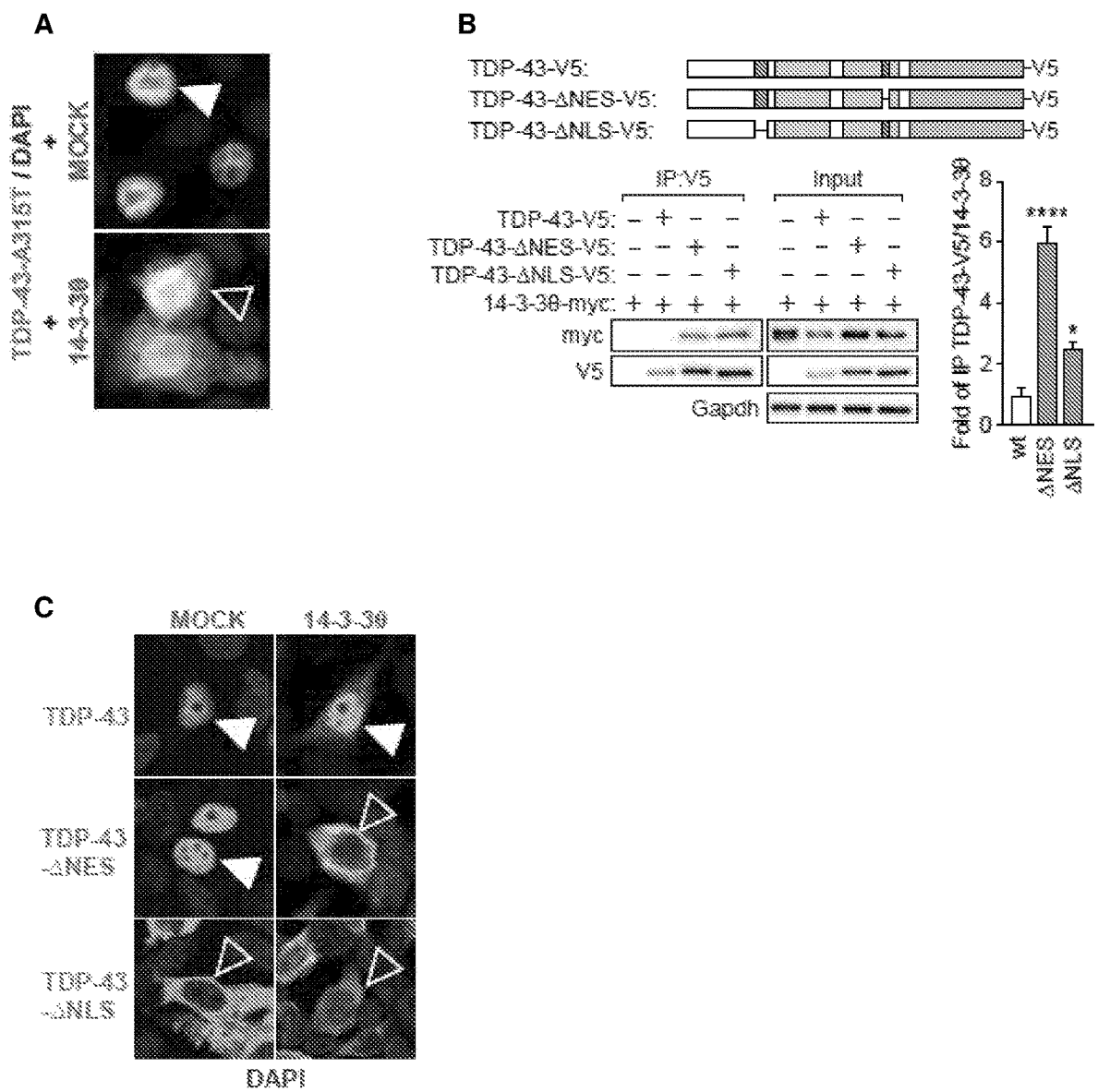
FIG. 3. (A) A315T mutant TDP-43, when expressed alone, localizes to the nucleus (+MOCK; arrowhead) but when expressed together with 14-3-3θ, A315T-TDP-43 colocalizes to the cytoplasm (open arrowhead). (B) Co-expression shows markedly enhanced IP of 14-3-3θ with TDP-43 lacking (Δ) NLS or NES compared to its non-mutant form (n=3). ****P<0.0001; *P<0.05. Error bars indicate SEM. (C) Co-expression of 14-3-3θ confers cytoplasmic localization of ΔNES TDP-43 (open arrowhead), which normally localizes to the nucleus (closed arrowhead). For comparison, cytoplasmic localization of ΔNLS TDP-43 and nuclear localization of non-mutant TDP-43 were not changed by 14-3-3θ.

To test whether a 14-3-3θ/TDP-43 interaction is disease relevant, the inventors expressed 14-3-3θ together with TDP-43 mutants in 293T HEK cells. Surprisingly, 14-3-3θ interacted significantly more with TDP-43 variants harboring pathogenic mutations, including the A315T mutation, a pathogenic variant associated with familial ALS and FTD (see FIG. 2). Co-expression of 14-3-3θ with TDP-43-A315T resulted in marked cytoplasmic co-localization (FIG. 3A). Nuclear localization (NLS) and nuclear export (NES) sequences mediate the predominant nuclear localization of TDP-43. Interestingly, 14-3-3θ showed strong interaction with both NES-deleted (ΔNES) and NLS-deleted (ΔNLS) variants of TDP-43 (FIG. 3B). While cytoplasmic localization of TDP-43-ΔNLS and nuclear localization of non-mutant TDP-43 were not altered by 14-3-3θ, TDP-43-ΔNES, which strictly localizes to the nucleus and forms nuclear aggregates when expressed in cells (Winton et al., 2008, *J Biol Chem* 283:13302-13309), was found almost exclusively in the cytoplasm when co-transfected with 14-3-3θ (FIG. 3C).

The findings described above demonstrate that the inventors have identified a novel interaction between 14-3-3θ and TDP-43 with augmented complex formation driving cytoplasmic localization of TDP-43 variants, including pathogenic variants.

The inventors then tested all 14-3-3 isoforms for potential interaction with TDP-43 by co-immunoprecipitation. TDP-43 was shown to interact with the 14-3-3η, 14-3-3γ and 14-3-3σ isoforms more strongly than with 14-3-3θ, but showed no overt interaction with 14-3-3ε, 14-3-3ζ and 14-3-3β (data not shown). The 14-3-3σ and 14-3-3ζ isoforms are not abundant in neurons. More importantly, only 14-3-3θ showed significantly stronger interaction with the TDP-43-A315T, and in particular TDP-43-ΔNES, variants compared to wild type TDP-43, while other interacting isoforms showed no enhanced interaction (in fact 14-3-3σ interacted less with TDP-43-ΔNES) (data not shown). Hence, only the interaction with 14-3-3θ changed with pathogenic variants of TDP-43.

Example 2—Interaction Motifs in 14-3-3θ Mediating Binding with TDP-43

14-3-3 dimers typically interact with phosphorylated forms of their interaction partner. However in contrast, in the case of TDP-43 the inventors found that phosphorylation-mimicking variants of TDP-43 interact less with 14-3-3θ supporting a non-canonical-type interaction (data not shown).

Figure 4:
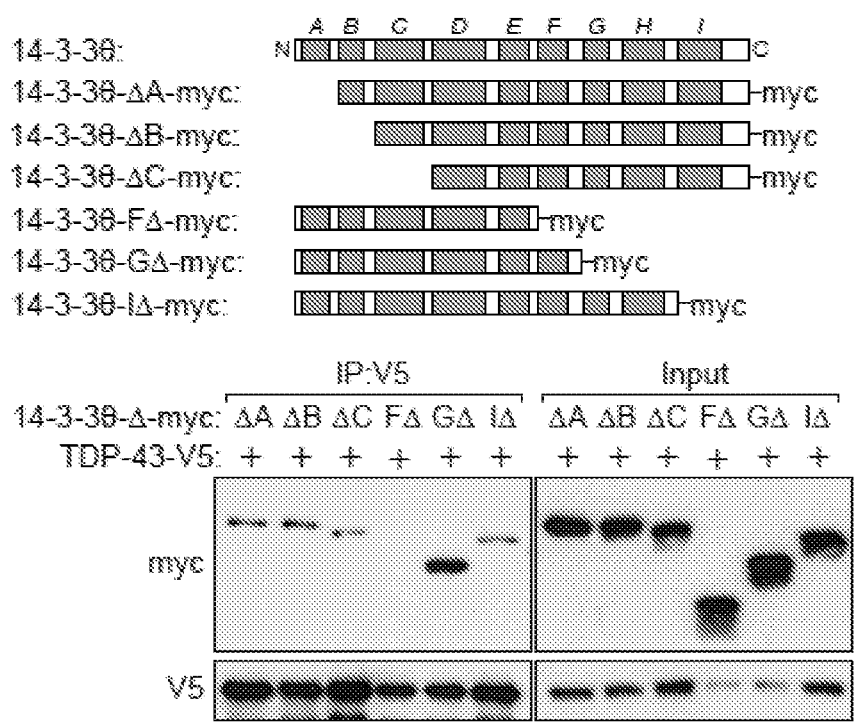
FIG. 4. N- and C-terminal truncation variants of 14-3-3θ immunoprecipitated with TDP-43 unless α-helix 6 (ΔF) was removed. Note the enhanced 14-3-3θ/TDP-43 immunoprecipitation in the absence of α-helices 7-9 (ΔG).

Structurally, 14-3-3θ harbors nine α-helices (see FIG. 4), with helices αC, αE, αG and αI contributing to canonical partner binding of 14-3-3θ dimers. To identify the interaction motif(s) in 14-3-3θ that mediate binding of TDP-43, the inventors truncated 14-3-3θ stepwise, revealing that the interaction is mediated by the sixth α-helix (αF) of 14-3-3θ (FIG. 4).

Figures 5, 6:
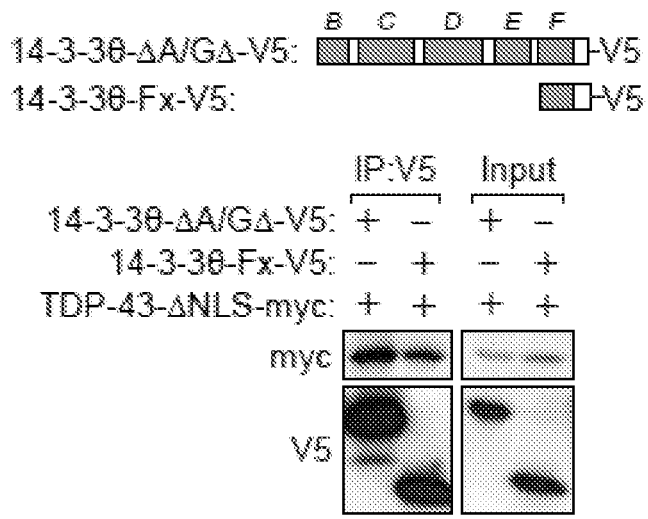
FIG. 5. Co-expression of 14-3-3θ α-helix 6 alone (14-3-3θ-Fx-V5) immunoprecipitated with TDP-43 similar to a GΔ variant of 14-3-3θ.
FIG. 6. Alignment of α-helix 6 of 14-3-3 isoforms corresponding to 14-3-3θ-Fx. Red box, 11 amino acid sequence unique to 14-3-3θ.

The inventors produced a construct including only α-helix 6 (αF) of 14-3-3θ (30 amino acid sequence shown in SEQ ID NO:2; corresponding to amino acids 135-164 of the wild type human TDP-43 sequence), terming this construct 'Fx'. Expressing Fx co-precipitated TDP-43 (FIG. 5), but failed to pull down known 14-3-3θ interaction partners YES-associated protein (YAP) and FOXO1 (data not shown), further supporting a non-canonical interaction between 14-3-3θ and TDP-43. The α-helix 6 (αF) of 14-3-3θ harbors a ten amino acid motif that is unique to 14-3-3θ over other 14-3-3 isoforms (FIG. 6) that is presented on opposing surfaces of the 14-3-3θ dimers and different from the conical interaction sites in the center of the molecule, explaining the unconventional interaction with TDP-43.

Example 3—Effects of Increased 14-3-3θ Expression In Vivo

Figure 7:
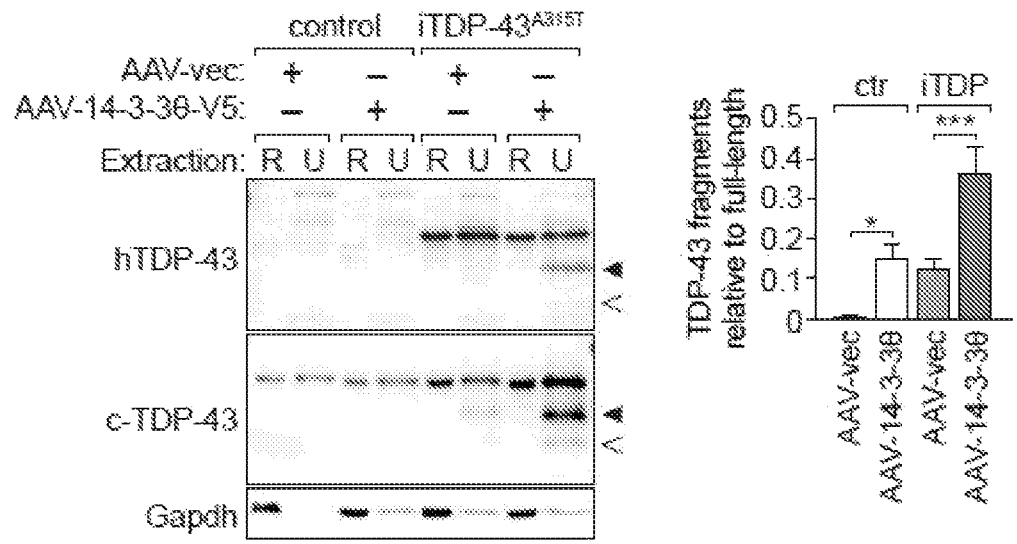
FIG. 7. (A) AAV-mediated expression of 14-3-3θ-V5 in the hippocampus resulted in insolubility and fragmentation (arrowheads) of TDP-43 in control (ctr) and iTDP-43$^{A315T}$ mice, respectively. Quantification of TDP-43 fragment levels from independent experiments (n=6). ***P<0.001; *P<0.05. Error bars indicate SEM. (B) Quantification of hTDP-43 expressing neurons in the hippocampus CA1 region of AAV-vec (vector) and AAV-14-3-3θ-V5 injected iTDP-43$^{A315T}$ mice. **P<0.01. Error bars indicate SEM.
Figure 7:
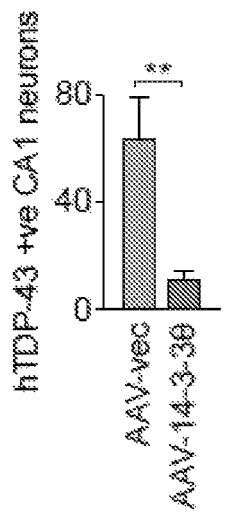

To study the effects of increased 14-3-3θ levels in vivo, the inventors used an adeno-associated virus (AAV) to express 14-3-3θ in the hippocampus of three month old non-transgenic mice and iTDP-43$^{A315T}$ mice. Increasing neuronal 14-3-3θ levels resulted in accumulation of insoluble TDP-43 fragments in non-transgenic mice, and more so in iTDP-43$^{A315T}$ mice (FIG. 7A). Furthermore, AAV-14-3-3θ-injected iTDP-43$^{A315T}$ mice showed substantial loss of hTDP-43-expressing hippocampal neurons compared to controls (FIG. 7B). Thus, increasing 14-3-3θ levels in vivo caused disease-like insolubility and fragmentation of endogenous and transgenic TDP-43, further exacerbating neuropathological phenotypes in iTDP-43$^{A315T}$ mice.

The inventors also tested whether long-term AAV-mediated over-expression of 14-3-3θ in spinal cords of naïve C57B1/6 mice results in altered endogenous TDP-43 and functional deficits. Histopathological analysis of spinal cords after 10 months of 14-3-3θ overexpression revealed cytoplasmic accumulation of TDP-43 in 14-3-3θ overexpressing anterior horn motor neurons, while non-expressing or GFP control cells presented with exclusively nuclear TDP-43 (data not shown). Thus, chronically increased 14-3-3θ levels compromised TDP-43 localization in motor neurons and resulted in functional motor deficits.

Example 4-14-3-3θ-Fx Targeted Degradation of Pathological TDP-43

Figure 8:
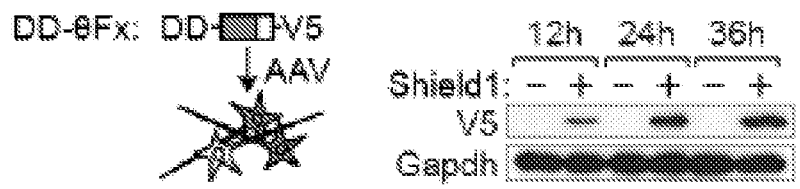
FIG. 8. (A) Amino acids 135-164 of 14-3-3θ with C-terminal degeneration domain (DD) and N-terminal V5 tag (DD-θFx) when expressed in primary neurons spontaneously degrade unless stabilized with Shield1 treatment. (B) DD-θFx reduced the levels of co-expressed A315T mutant human (h) TDP-43 in primary neurons (n=4). Graph: left hand column, TDP-43; right hand column, TDP-43+DD-θFx. **, P<0.01. Error bars indicate SEM.
Figure 8:
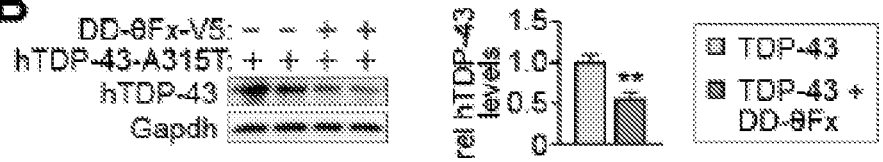
Figure 9:
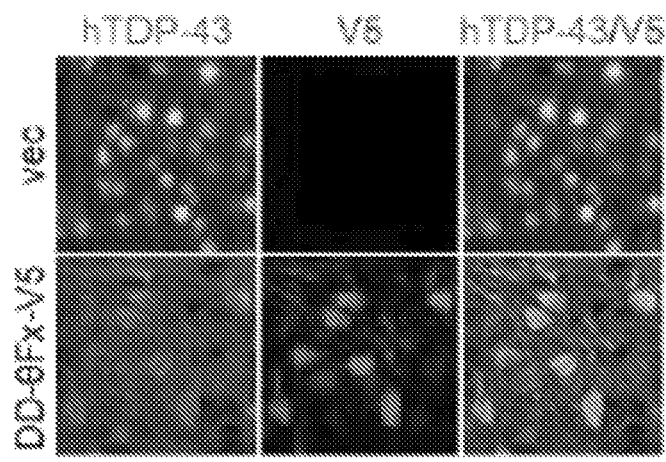
FIG. 9. (A) Predominantly nuclear hTDP-43 in the cortex of vec injected iTDP-43$^{A315T}$ mice was markedly reduced in DD-θFx-expressing neurons. (B) Reduced TDP-43 levels in iTDP-43$^{A315T}$ brains expressing DD-θFx from birth (n=3). mCherry and V5 confirmed AAV-mediated expression. Note that DD-θFx expressed higher in iTDP-43$^{A315T}$ than control mice. Graph: left hand column, P0:iTDP-43+vec; right hand column, P0:iTDP-43+DD-θFx. *, P<0.05. Error bars indicate SEM.
Figure 9:
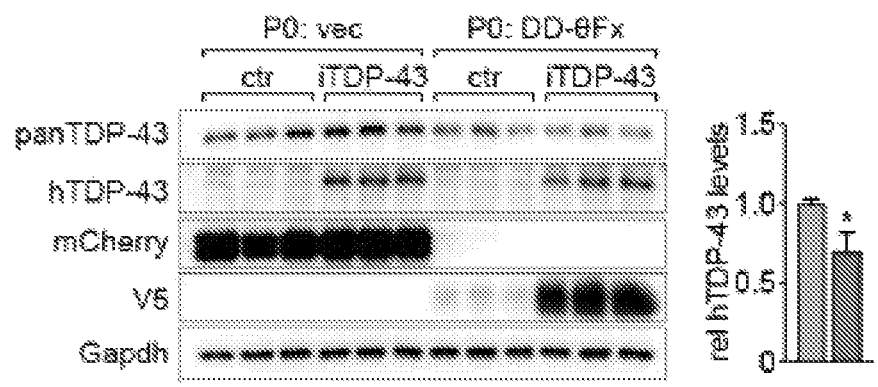
Figure 10:
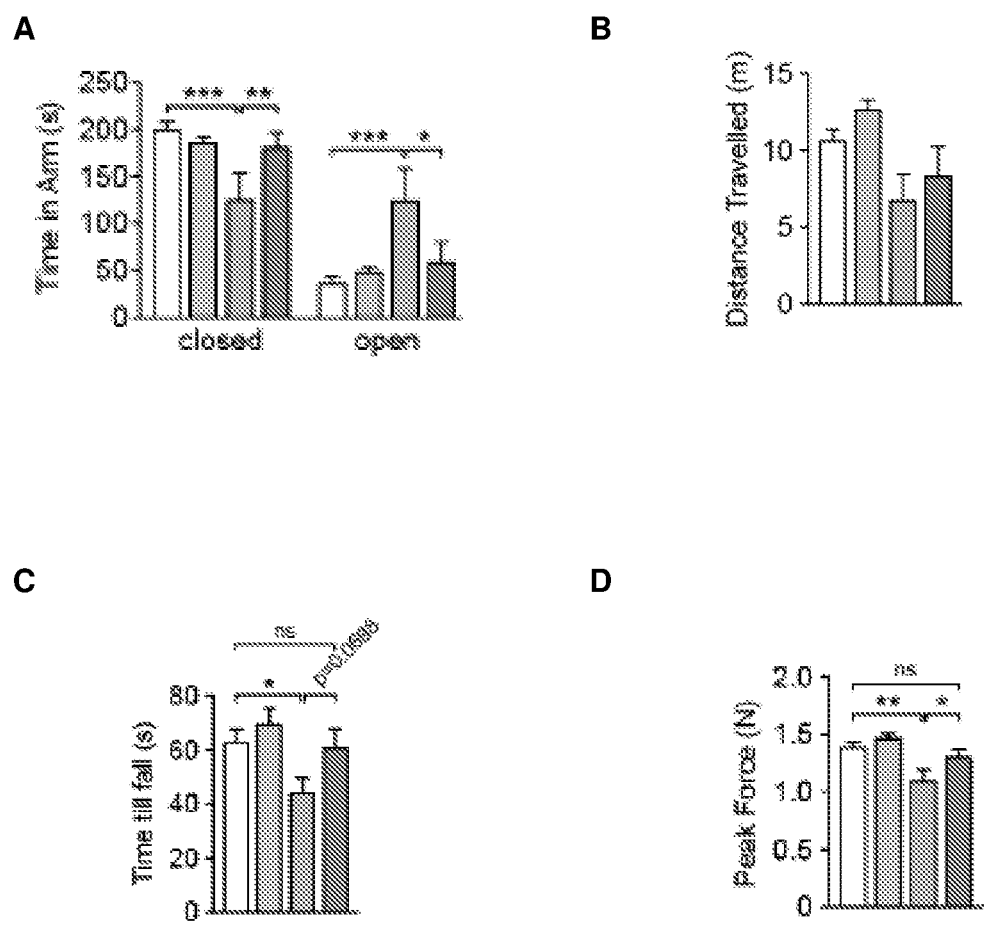
FIG. 10. (A) Disinhibition (as reflected by increased open arm time in the elevated plus maze) of vec-treated iTDP-43$^{A315T}$ mice was significantly reduced upon DD-θFx expression (n=8). (B) Increased activity (as reflected by higher distance travelled in the open field) of vec-treated iTDP-43$^{A315T}$ mice was significantly reduced upon DD-θFx expression (n=8). (C) Reduced motor performance (as reflected by short time to fall off rotating rod) of vec-treated iTDP-43$^{A315T}$ mice was comparable to ctr mice upon DD-θFx expression (n=8). (D) Reduced grip strength of vec-treated iTDP-43$^{A315T}$ mice was significantly higher upon DD-θFx expression (n=8). For (A)-(D): first column, P0:ctr+vec; second column, P0:ctr+DD-θFx; third column, P0:iTDP-43+vec; fourth column, P0:iTDP-43+DD-θFx. vec=vector. ctr=control. *P<0.001; P<0.01; *P<0.05; ns, not significant. Error bars indicate SEM.

The unique mode of interaction between 14-3-3θ and TDP-43 together with the preference of 14-3-3θ for aberrant forms of TDP-43 prompted the inventors to explore whether 14-3-3θ could be used to target pathological TDP-43 therapeutically. The inventors designed a construct comprising 14-3-3θ-Fx (Example 2) fused to a C-terminal degradation domain (DD) from a PTuner plasmid (Clonetech) and a N-terminal V5 tag for detection (hereby termed 'DD-θFx'). DD-θFx was shown to accumulate in primary neurons only in the presence of the stabilizing compound Shield1, confirming efficient DD-induced degradation in neurons (FIG. 8A). Co-expression of DD-θFx with A315T-mutant human TDP-43 (hTDP-43) in neurons caused significant reduction of hTDP-43 levels, consistent with induced degradation (FIG. 8B). Furthermore, AAV-mediated expression of DD-θFx in brains of iTDP-43$^{A315T}$ mice resulted in mutually exclusive expression of transgenic hTDP-43 to DD-θFx (FIG. 9A) and reduced TDP-43 levels (FIG. 9B). This suggests clearance of transgenic hTDP-43 mediated by DD-θFx degradation. Turnover of DD-θFx was higher in control mice than iTDP-43$^{A315T}$ mice, likely due to presence of TDP-43 aggregates in iTDP-43$^{A315T}$ mice. Functional assessment of DD-θFx-expressing iTDP-43$^{A315T}$ mice showed less disinhibition, less hyperactivity, reduced motor deficits and increased muscle strength as compared to control vector-injected iTDP-43$^{A315T}$ mice (FIG. 10). Hence, DD-θFx induces targeted degradation of pathogenic TDP-43 in neurons and prevented deficits in iTDP-43$^{A315T}$ mice.

Figure 11:
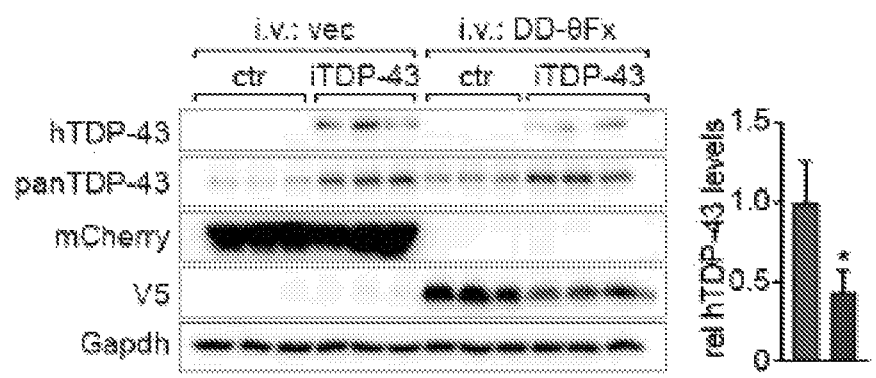
FIG. 11. (A) Reduced transgenic hTDP-43 levels in iTDP-43$^{A315T}$ mice expressing DD-θFx-V5 as compared to mCherry (n=3). Graph: left hand column, i.v.:iTDP-43+vec; right hand column, i.v.:iTDP-43+DD-θFx. vec=vector. *P<0.05. Error bars indicate SEM. (B) Staining of brain from vec- and DD-θFx-expressing mice showed reduced number of hTDP-43-positive cells in the hippocampus (n=6). Graph: left hand column, i.v.:iTDP-43+vec; right hand column, i.v.:iTDP-43+DD-θFx. vec=vector. **P<0.01. Error bars indicate SEM.
Figure 11:
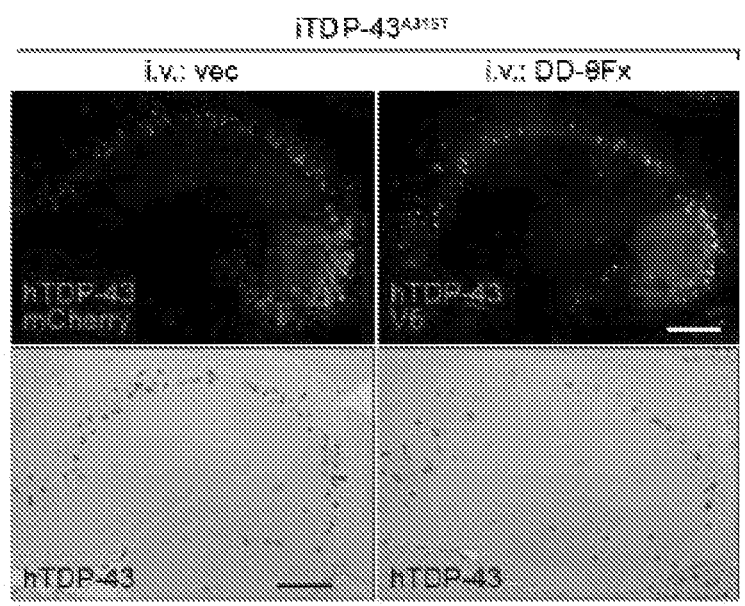
Figure 12:
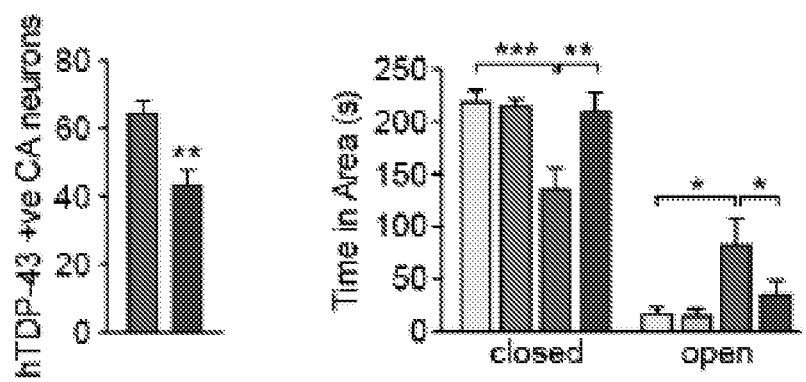
FIG. 12. Disinhibition of vec-treated iTDP-43$^{A315T}$ mice was significantly ameliorated upon DD-θFx expression (n=6). First column, i.v.:ctr+vec; second column, i.v.:ctr+DD-θFx; third column, i.v.:iTDP-43+vec; fourth column, i.v.:iTDP-43+DD-θFx. vec=vector. ctr=control. *P<0.001; P<0.01; *P<0.05. Error bars indicate SEM.

The inventors then used the neurotrophic AAV serotype AAV.PHP.B (Deverman et al., 2016, *Nat Biotechnol* 34:204-209), allowing systemic delivery of DD-θFx (or controls) to CNS neurons in three month old iTDP-43$^{A315T}$ mice with established deficits. Western blotting confirmed reduction of hTDP-43 in DD-θFx-expressing iTDP-43$^{A315T}$ mice compared to controls (FIG. 11A). This resulted in comparable and reproducible DD-θFx and control vector expression patterns throughout the CNS within two weeks (FIG. 11B). Importantly, a 32.6±6.6% reduction was observed in hTDP-43-expressing neurons in the absence of overt cell loss. Furthermore, DD-θFx co-localized with hTDP-43 in remaining neurons, many of which showed only weak transgenic TDP-43 staining. Next, three and a half month old iTDP-43$^{A315T}$ mice (i.e. two weeks after DD-θFx AAV delivery) were functionally assessed. At this age, untreated iTDP-43$^{A315T}$ mice present profound impairments (Ke et al., 2015 *Acta Neuropathol* 130:661-678). Notably, DD-θFx expression improved disinhibition of iTDP-43$^{A315T}$ mice (FIG. 12). Expression of control vectors had no effect on the deficits of iTDP-43$^{A315T}$ mice in these tasks. DD-θFx left performance of control mice unaffected. Taken together, neuronal DD-θFx expression decreased TDP-43 levels and improved established functional deficits of iTDP-43$^{A315T}$ mice. This data suggests that pathological TDP-43 can be targeted and cleared using specific interaction peptides, resembling a potential new avenue of treating ALS and FTD.

Example 5—DD-θFx Prevented Deficits Induced by Expression of Human Wild Type TDP-43 in Mice The inventors then investigated the effect of DD-θFx expression in a mouse model of sporadic ALS, based on AAV-mediated expression of non-mutant hTDP-43 in CNS neurons. The inventors used the neurotropic AAV9 serotype, AAV.PHP.B, allowing systemic delivery and uniform expression in CNS neurons (Deverman et al., 2016, *Nat Biotechnol* 34:204-209) via temporal vein injection in naïve newborn C57Bl/6 mice. The effect of DD-θFx was investigated by co-injection (AAV-DD-θFx) at birth in mice injected with either native hTDP-43 (AAV-hTDP-43) or AAV vector alone (AAV-ctr).

Figure 13:
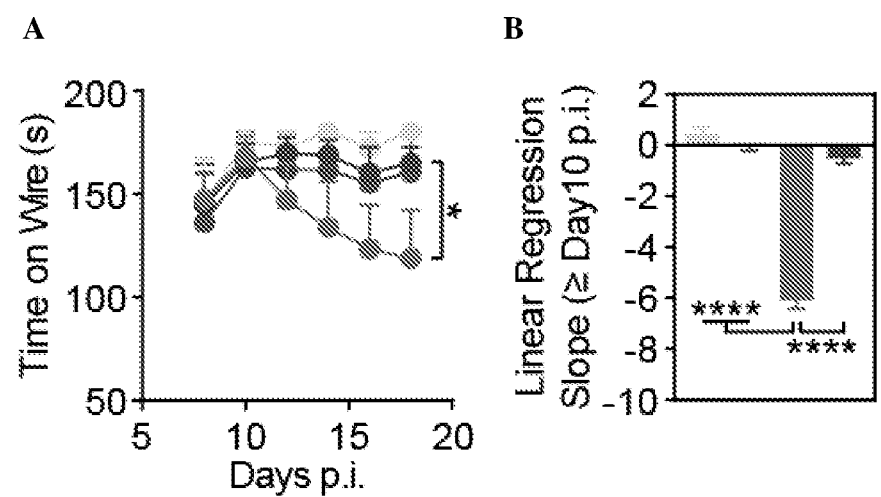
FIG. 13. Progressive decline in body strength, as reflected by reduced inverted wire times (A) and corresponding linear regression slope differences (B) in vec-treated AAV-hTDP-43 mice as comparable to AAV-DD-θFx-injected AAV-hTDP mice and controls (n=10). B: first column, AAV-vec+AAV-vec; second column, AAV-vec+AAV-DD-θFx; third column, AAV-hTDP-43+AAV-vec; fourth column, AAV-hTDP-43+AAV-DD-θFx. * P<0.05, **** P<0.0001. Error bars indicate SEM.
Figure 14:
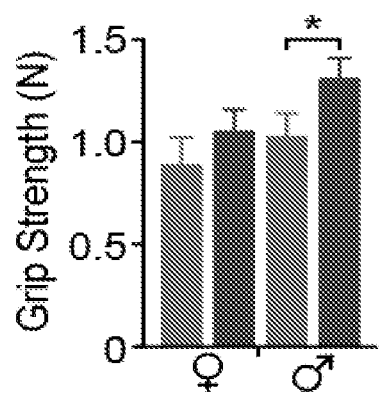
FIG. 14. Reduced grip strength in AAV-vec-treated AAV-hTDP-43 mice compared to AAV-DD-θFx-injected AAV-hTDP-43 mice (n=7). First column, AAV-hTDP-43+AAV-vec female mice; second column, AAV-hTDP-43+AAV-DD-θFx female mice; third column, AAV-hTDP-43+AAV-vec male mice; fourth column, AAV-hTDP-43+AAV-DD-θFx male mice. * P<0.05. Error bars indicate SEM.
Figure 15:
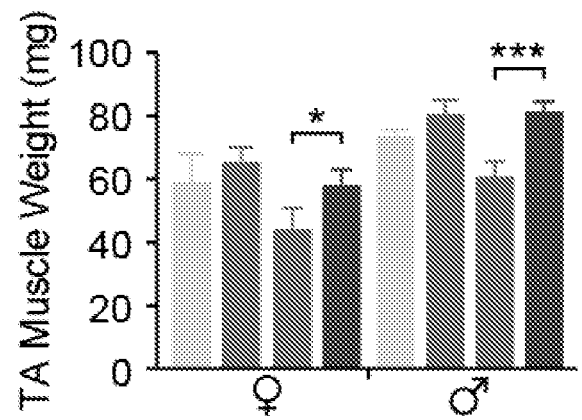
FIG. 15. Atrophy of tibialis anterior (TA) muscle, represented by reduced weight, in female and male vec-treated AAV-hTDP-43 mice as comparable to AAV-DD-θFx-injected AAV-hTDP mice (n=3-7). For female and male mice: first column, AAV-vec +AAV-vec; second column, AAV-vec+AAV-DD-θFx; third column, AAV-hTDP-43+AAV-vec; fourth column, AAV-hTDP-43+AAV-DD-θFx. * P<0.05, *** P<0.001. Error bars indicate SEM.

Until 10 weeks of age, AAV-hTDP-43 and AAV-ctr showed comparable performance fortnightly inverted wire testing (FIG. 13), suggesting comparable strength. Thereafter, performance in the inverted wire testing progressively declined in mice administered AAV-hTDP-43, but this was fully prevented when mice were co-treated with AAV-DD-θFx at birth (FIG. 13). This result was corroborated by direct assessment of grip strength, which was significantly reduced in male AAV-hTDP-43 mice as compared with AAV-ctr mice, and was prevented by DD-θFx co-treatment (FIG. 14). A comparable trend was observed in female mice. Further, tibialis anterior muscle weights of 19 weeks old female and male AAV-hTDP-43 mice were significantly reduced as compared with the respective controls (FIG. 15). These results demonstrate that DD-θFx prevented deficits induced by non-mutant TDP-43 expression in mice.

The invention claimed is:

1. An isolated peptide comprising a fragment of human 14-3-3θ, wherein said fragment is within α helix 6 (αF) of human 14-3-3θ and comprises the amino acid sequence of SEQ ID NO: 1.

2. The peptide of claim 1 comprising the amino acid sequence of SEQ ID NO:2, or a sequence at least about 75% identical to the sequence of SEQ ID NO:2.

3. A chimeric molecule comprising a peptide fragment of human 14-3-3θ, wherein said fragment is within a helix 6 (αF) of human 14-3-3θ and comprises the amino acid sequence of SEQ ID NO: 1 linked to a protein destabilization domain sequence.

4. A method for treating or ameliorating at least one symptom of, a neurodegenerative disease associated with TDP-43 pathology, the method comprising administering to a subject in need thereof an effective amount of a peptide fragment of human 14-3-3θ, wherein said fragment is within a helix 6 (αF) of human 14-3-3θ and comprises the amino acid sequence of SEQ ID NO: 1 or a nucleic acid molecule encoding said peptide fragment.

5. The method of claim 4, wherein the neurodegenerative disease is selected from amyotrophic lateral sclerosis (ALS) and frontotemporal dementia (FTD).

6. The method of claim 4, wherein the at least one symptom comprises disinhibition, hyperactivity, motor deficits or reduced muscle strength.

7. The method of claim 4, wherein the nucleic acid molecule encodes the peptide fragment comprising SEQ ID NO: 1.

8. The method of claim 4, wherein the peptide fragment comprises the amino acid sequence of SEQ ID NO: 2, or a sequence at least about 75% identical to the sequence of SEQ ID NO:2.

9. The method of claim 4, comprising administering a nucleic acid molecule encoding the peptide fragment comprising the amino acid sequence of SEQ ID NO:2, or a sequence at least about 75% identical to the sequence of SEQ ID NO: 2.

10. The method of claim 9, wherein the nucleic acid molecule encoding the peptide fragment comprising the amino acid sequence of SEQ ID NO: 2, or a sequence at least about 75% identical thereto comprises the nucleotide sequence of SEQ ID NO:5 or a nucleotide sequence at least about 70% identical to the sequence of SEQ ID NO:5.

11. The method of claim 4, wherein the peptide fragment is linked to a protein destabilization domain sequence.

12. The method of claim 11, wherein the protein destabilization domain sequence comprises a rapamycin-binding protein FKBP12, ubiquitin, a PEST (proline-rich, glutamic acid-rich, serine-rich and threonine-rich) sequence, a cyclin destruction box and/or a hydrophobic stretch of amino acids.

13. The method of claim 4, wherein the method comprises administering to the subject a genetic construct encoding the peptide fragment comprising the sequence of SEQ ID NO:1 operably linked to a nucleotide sequence encoding a protein destabilization domain.

14. The method of claim 4, wherein the peptide fragment comprises the amino acid sequence of SEQ ID NO:2.

15. The method of claim 4, comprising the administration of a nucleic acid molecule encoding the peptide fragment comprising the amino acid sequence of SEQ ID NO:2.

16. The method of claim 15, wherein the nucleic acid molecule comprises the nucleotide sequence of SEQ ID NO:5 or a nucleotide sequence at least about 70% identical to the sequence of SEQ ID NO:5.

17. The method of claim 4, wherein the peptide fragment is linked to a protein destabilization domain sequence.

18. The method of claim 17, wherein the protein destabilization domain sequence comprises a rapamycin-binding protein FKBP12, ubiquitin, a PEST (proline-rich, glutamic acid-rich, serine-rich and threonine-rich) sequence, a cyclin destruction box and/or a hydrophobic stretch of amino acids.

19. The method of claim 4, wherein the method comprises administering to the subject a genetic construct encoding a peptide fragment of human 14-3-3θ, wherein said fragment is within a helix 6 (aF) of human 14-3-3θ and comprises the amino acid sequence of SEQ ID NO: 1 operably linked to a nucleotide sequence encoding a protein destabilization domain.

20. The method of claim 19, wherein the protein destabilization domain sequence comprises a rapamycin-binding protein FKBP12, ubiquitin, a PEST (proline-rich, glutamic acid-rich, serine-rich and threonine-rich) sequence, a cyclin destruction box and/or a hydrophobic stretch of amino acids.

21. The method of claim 7, wherein the nucleic acid molecule comprises the nucleotide sequence of SEQ ID NO:4.

22. A method for treating or ameliorating at least one symptom of, a neurodegenerative disease associated with TDP-43 pathology comprising administering to a subject in need thereof an effective amount of the chimeric molecule of claim 3, or a polynucleotide encoding said chimeric molecule.

* * * * *

SEQUENCE LISTING

```
<160> NUMBER OF SEQ ID NOS: 20

<210> SEQ ID NO 1
<211> LENGTH: 11
<212> TYPE: PRT
<213> ORGANISM: Homo sapiens

<400> SEQUENCE: 1

Arg Lys Gln Thr Ile Asp Asn Ser Gln Gly Ala
1               5                   10

<210> SEQ ID NO 2
<211> LENGTH: 30
<212> TYPE: PRT
<213> ORGANISM: Homo sapiens

<400> SEQUENCE: 2

Gly Asp Asp Arg Lys Gln Thr Ile Asp Asn Ser Gln Gly Ala Tyr Gln
1               5                   10                  15

Glu Ala Phe Asp Ile Ser Lys Lys Glu Met Gln Pro Thr His
            20                  25                  30

<210> SEQ ID NO 3
<211> LENGTH: 245
<212> TYPE: PRT
<213> ORGANISM: Homo sapiens

<400> SEQUENCE: 3

Met Glu Lys Thr Glu Leu Ile Gln Lys Ala Lys Leu Ala Glu Gln Ala
1               5                   10                  15

Glu Arg Tyr Asp Asp Met Ala Thr Cys Met Lys Ala Val Thr Glu Gln
            20                  25                  30
```

Gly Ala Glu Leu Ser Asn Glu Glu Arg Asn Leu Leu Ser Val Ala Tyr
            35                  40                  45

Lys Asn Val Val Gly Gly Arg Ser Ala Trp Arg Val Ile Ser Ser
 50                  55                  60

Ile Glu Gln Lys Thr Asp Thr Ser Asp Lys Leu Gln Leu Ile Lys
 65                  70                  75                  80

Asp Tyr Arg Glu Lys Val Glu Ser Glu Leu Arg Ser Ile Cys Thr Thr
                85                  90                  95

Val Leu Glu Leu Leu Asp Lys Tyr Leu Ile Ala Asn Ala Thr Asn Pro
            100                 105                 110

Glu Ser Lys Val Phe Tyr Leu Lys Met Lys Gly Asp Tyr Phe Arg Tyr
            115                 120                 125

Leu Ala Glu Val Ala Cys Gly Asp Asp Arg Lys Gln Thr Ile Asp Asn
130                 135                 140

Ser Gln Gly Ala Tyr Gln Glu Ala Phe Asp Ile Ser Lys Lys Glu Met
145                 150                 155                 160

Gln Pro Thr His Pro Ile Arg Leu Gly Leu Ala Leu Asn Phe Ser Val
                165                 170                 175

Phe Tyr Tyr Glu Ile Leu Asn Asn Pro Glu Leu Ala Cys Thr Leu Ala
            180                 185                 190

Lys Thr Ala Phe Asp Glu Ala Ile Ala Glu Leu Asp Thr Leu Asn Glu
            195                 200                 205

Asp Ser Tyr Lys Asp Ser Thr Leu Ile Met Gln Leu Leu Arg Asp Asn
        210                 215                 220

Leu Thr Leu Trp Thr Ser Asp Ser Ala Gly Glu Glu Cys Asp Ala Ala
225                 230                 235                 240

Glu Gly Ala Glu Asn
            245

<210> SEQ ID NO 4
<211> LENGTH: 33
<212> TYPE: DNA
<213> ORGANISM: Homo sapiens

<400> SEQUENCE: 4
cgaaaacaaa cgatagataa ttcccaagga gct                               33

<210> SEQ ID NO 5
<211> LENGTH: 90
<212> TYPE: DNA
<213> ORGANISM: Homo sapiens

<400> SEQUENCE: 5
ggtgatgatc gaaaacaaac gatagataat tcccaaggag cttaccaaga ggcatttgat   60
ataagcaaga aagagatgca acccacacac                                    90

<210> SEQ ID NO 6
<211> LENGTH: 58
<212> TYPE: DNA
<213> ORGANISM: Artificial Sequence
<220> FEATURE:
<223> OTHER INFORMATION: Synthetic sequence

<400> SEQUENCE: 6
ccggcagttg cttagagaca acctactcga gtaggttgtc tctaagcaac tgttttg      58

<210> SEQ ID NO 7

```
<211> LENGTH: 22
<212> TYPE: DNA
<213> ORGANISM: Artificial Sequence
<220> FEATURE:
<223> OTHER INFORMATION: Synthetic sequence

<400> SEQUENCE: 7
gctaaaacgg cttttgatga gg                                              22

<210> SEQ ID NO 8
<211> LENGTH: 21
<212> TYPE: DNA
<213> ORGANISM: Artificial Sequence
<220> FEATURE:
<223> OTHER INFORMATION: Synthetic sequence

<400> SEQUENCE: 8
gtgccctgga tgcctttagt t                                               21

<210> SEQ ID NO 9
<211> LENGTH: 20
<212> TYPE: DNA
<213> ORGANISM: Artificial Sequence
<220> FEATURE:
<223> OTHER INFORMATION: Synthetic sequence

<400> SEQUENCE: 9
ctccagtcct ccgcgaaaat                                                 20

<210> SEQ ID NO 10
<211> LENGTH: 20
<212> TYPE: DNA
<213> ORGANISM: Artificial Sequence
<220> FEATURE:
<223> OTHER INFORMATION: Synthetic sequence

<400> SEQUENCE: 10
gagagttcgt gtccctgctc                                                 20

<210> SEQ ID NO 11
<211> LENGTH: 20
<212> TYPE: DNA
<213> ORGANISM: Artificial Sequence
<220> FEATURE:
<223> OTHER INFORMATION: Synthetic sequence

<400> SEQUENCE: 11
ggcggtcttc ggtttccttc                                                 20

<210> SEQ ID NO 12
<211> LENGTH: 21
<212> TYPE: DNA
<213> ORGANISM: Artificial Sequence
<220> FEATURE:
<223> OTHER INFORMATION: Synthetic sequence

<400> SEQUENCE: 12
gttcagctcg gtcacgttct t                                               21

<210> SEQ ID NO 13
<211> LENGTH: 19
<212> TYPE: DNA
<213> ORGANISM: Artificial Sequence
<220> FEATURE:
<223> OTHER INFORMATION: Synthetic sequence

<400> SEQUENCE: 13
```

```
cgcaccccat tcgtttagg                                                    19

<210> SEQ ID NO 14
<211> LENGTH: 21
<212> TYPE: DNA
<213> ORGANISM: Artificial Sequence
<220> FEATURE:
<223> OTHER INFORMATION: Synthetic sequence

<400> SEQUENCE: 14
attctgctct tcaccatcac c                                                 21

<210> SEQ ID NO 15
<211> LENGTH: 20
<212> TYPE: DNA
<213> ORGANISM: Artificial Sequence
<220> FEATURE:
<223> OTHER INFORMATION: Synthetic sequence

<400> SEQUENCE: 15
ctacgatcac gtccaacccg                                                   20

<210> SEQ ID NO 16
<211> LENGTH: 19
<212> TYPE: DNA
<213> ORGANISM: Artificial Sequence
<220> FEATURE:
<223> OTHER INFORMATION: Synthetic sequence

<400> SEQUENCE: 16
gtcaaacgct tctggctgc                                                    19

<210> SEQ ID NO 17
<211> LENGTH: 20
<212> TYPE: DNA
<213> ORGANISM: Artificial Sequence
<220> FEATURE:
<223> OTHER INFORMATION: Synthetic sequence

<400> SEQUENCE: 17
acaacctgac actgtggacg                                                   20

<210> SEQ ID NO 18
<211> LENGTH: 20
<212> TYPE: DNA
<213> ORGANISM: Artificial Sequence
<220> FEATURE:
<223> OTHER INFORMATION: Synthetic sequence

<400> SEQUENCE: 18
cctttggagc aagaacagcg                                                   20

<210> SEQ ID NO 19
<211> LENGTH: 18
<212> TYPE: DNA
<213> ORGANISM: Artificial Sequence
<220> FEATURE:
<223> OTHER INFORMATION: Synthetic sequence

<400> SEQUENCE: 19
gtgaaggtcg gtgtgaac                                                     18

<210> SEQ ID NO 20
<211> LENGTH: 21
<212> TYPE: DNA
```

```
<213> ORGANISM: Artificial Sequence
<220> FEATURE:
<223> OTHER INFORMATION: Synthetic sequence

<400> SEQUENCE: 20
atctccactt tgccactgca a                                               21
```